United States Patent [19]
Choi et al.

[11] Patent Number: 5,789,444
[45] Date of Patent: Aug. 4, 1998

[54] METHOD OF REDUCING GLUTAMATE NEUROTOXICITY WITH ANTHRANILIC ACID DERIVATIVES

[75] Inventors: Dennis Wonkyu Choi, St. Louis, Mo.; Sandra Jeanne Hewett, Avon, Conn.

[73] Assignee: Washington University, St. Louis, Mo.

[21] Appl. No.: 706,584

[22] Filed: Sep. 5, 1996

Related U.S. Application Data

[60] Provisional application No. 60/005,060, Oct. 6, 1995 and provisional application No. 60/007,355, Nov. 20, 1995.

[51] Int. Cl.⁶ .......................... A61K 31/195; A61K 31/24
[52] U.S. Cl. ................................. 514/567; 514/535
[58] Field of Search ............................. 514/567, 535

[56] References Cited

U.S. PATENT DOCUMENTS

| | | |
|---|---|---|
| 3,138,636 | 6/1964 | Scherrer . |
| 3,144,387 | 8/1964 | Jones . |
| 3,313,848 | 4/1967 | Scherrer et al. . |

OTHER PUBLICATIONS

Hall et al., J. Neurosurg., 64:951–961 (1986).

Buccie et al., Surg. Neurol., 33:12–14 (1990).

Faden et al, Derwent Drug File Abstracts, vol. 92, abstract No. 21000, 1992.

Hall et al, Chemical Abstracts, vol. 105, abstract No. 91569, 1986.

*Primary Examiner*—William R. A. Jarvis
*Attorney, Agent, or Firm*—George W. Johnston; Dennis P. Tramaloni; Bruce A. Pokras

[57] ABSTRACT

A method of reducing neurotoxic injury due to acute or chronic neurological insults by administering an anthranilic acid derivative is disclosed.

67 Claims, 8 Drawing Sheets

METHOD OF REDUCING GLUTAMATE NEUROTOXICITY WITH ANTHRANILIC ACID DERIVATIVES

This invention was made with U.S. government support under grant NS 30337 awarded by the National Institutes of Health. The U.S. government has certain rights to this invention.

This application claims priority to provisional application no. 60/005,060, filed Oct. 6, 1995 and provisional application no. 60/007,355, filed Nov. 20, 1995.

BACKGROUND OF THE INVENTION

Glutamate is the major excitatory neurotransmitter in the brain and spinal cord, and mediates many normal neurological functions including cognition and movement. However, overstimulation of glutamate receptors, especially glutamate receptors of the N-methyl-D-aspartate ("NMDA") receptor subtype, is lethal to neurons as demonstrated by in vitro and in vivo studies (Olney, 1986; Coyle et al., 1981; Choi, 1991). Thus, glutamate release triggered by a number of acute neurological insults such as hypoxia-ischemia (such as occurs during stroke), hypoglycemia, epilepsy or trauma would be a causative factor in the pathogenesis of brain injury. In addition, the glutamate release which occurs during the course of neurodegenerative disorders such as Huntington's and Alzheimer's disease, amyotropic lateral sclerosis, and AIDS dementia (Meldrum, 1985; Rothman and Olney, 1987, Choi, 1988b; Meldrum and Garthwaite, 1990; Lipton, 1992) would also be a causative factor in the pathogenesis of brain injury in patients with those diseases. Thus, it would be desirable to provide a means of protecting neurons from glutamate-induced neurotoxicity.

Selective antagonists of the NMDA subtype of glutamate receptor protect neurons from glutamate-induced neurotoxicity in both in vitro and in vivo models of hypoxic/ischemic brain injury (Goldberg et al. 1987; Choi, 1990). However, given the clinical context in which glutamate-induced neuronal injury occurs, i.e., after an acute neurological insult and receptor binding have occurred, compounds that prevent or inhibit glutamate neurotoxicity after initial receptor binding has occurred are desirable. The blockage of distal neurotoxic events set in motion by receptor overstimulation may be better tolerated than receptor antagonism per se over long periods of time.

SUMMARY OF THE INVENTION

We have discovered that compounds selected from the group consisting of:

I wherein $R_1$ is halogen or methyl; $R_2$ is halogen, lower alkyl, lower alkoxy, benzyloxy or $\beta,\beta,\beta$-trifluoroethoxy wherein at least one of $R_1$ and $R_2$ are halogen; $R_3$ is hydrogen, halogen or methyl; M is hydrogen, a pharmaceutically acceptable cation or lower-alkyl; and

II wherein $R_4$ is lower alkyl; and

III their pharmaceutically acceptable salts and pharmaceutically acceptable esters, inhibits glutamate-induced neurotoxicity.

Thus, the present invention provides a method of reducing neurotoxic injury by administering a compound of the formula I, II or III to a patient in need of such treatment in an amount sufficient to reduce said neurotoxic injury.

DETAILED DESCRIPTION OF THE INVENTION

Figure 1:
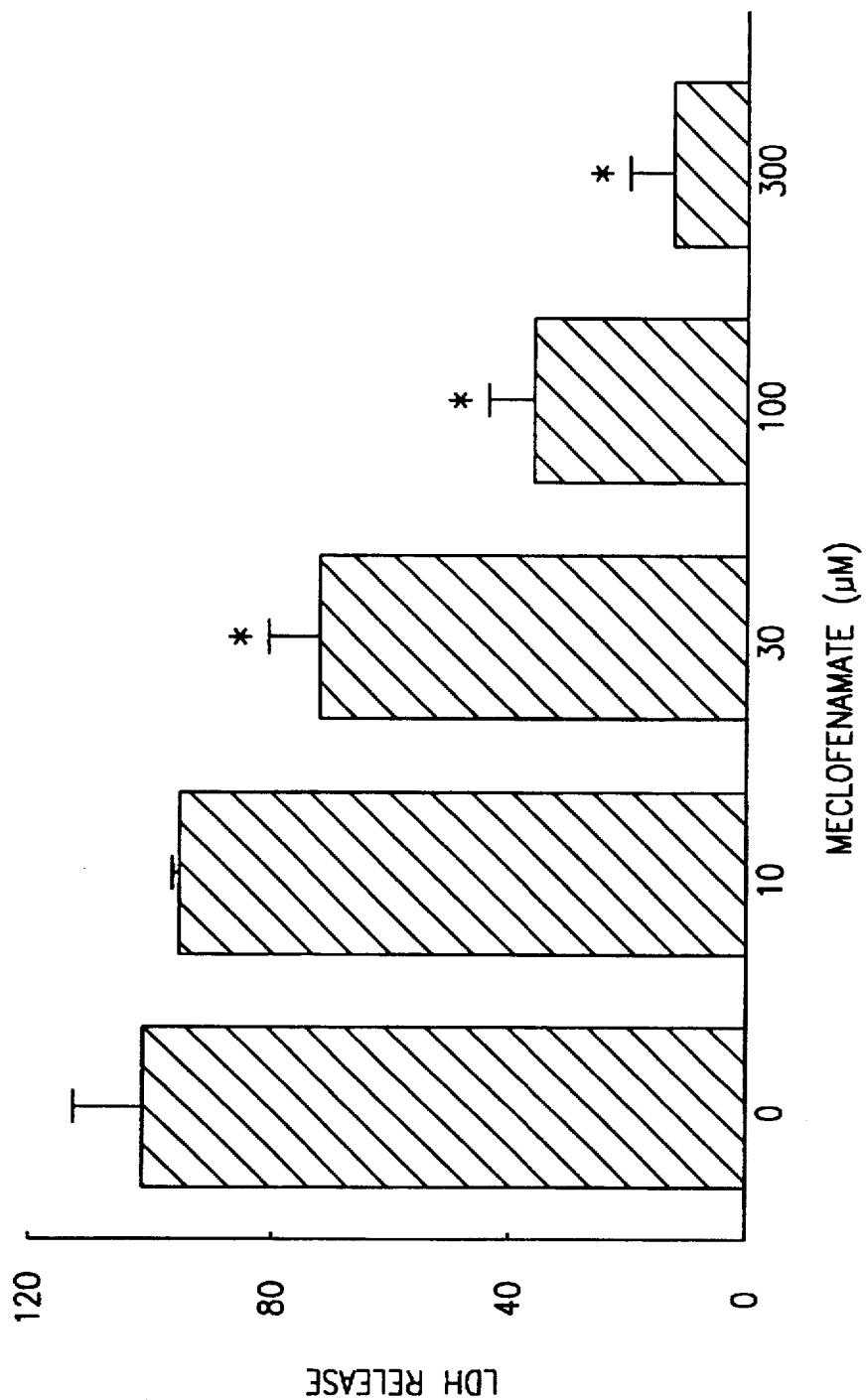
FIG. 1. Effect of meclofenamate sodium on NMDA-mediated excitotoxicity.

The present invention comprises a method of treating neurotoxic injury in a patient suffering said injury comprising administering to said patient a composition comprising an anthranilic acid derivative selected from the group consisting of:

I wherein $R_1$ is halogen or methyl; $R_2$ is halogen, lower alkyl, lower alkoxy, benzyloxy or $\beta,\beta,\beta$-trifluoroethoxy wherein at least one of $R_1$ and $R_2$ are halogen; $R_3$ is hydrogen, halogen or methyl; M is hydrogen, a pharmaceutically acceptable cation or lower-alkyl; and

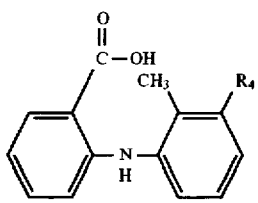

wherein $R_4$ is lower alkyl; and

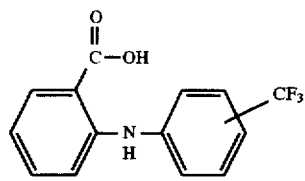

their pharmaceutically acceptable salts and pharmaceutically acceptable esters,
and a pharmaceutically acceptable carrier, wherein said anthranilic acid derivative is present in said composition in an amount sufficient to treat said neurotoxic injury.

The compounds of formula I are disclosed in U.S. Pat. No. 3,313,848 issued Apr. 11, 1967. The compounds of formula II are disclosed in U.S. Pat. No. 3,138,636 issued Jun. 23, 1964. The compounds of formula III are disclosed in U.S. Pat. No. 3,144,387 issued Aug. 11, 1964. The compounds of formulas I, II and III may be prepared by any conventional means, but are preferably prepared in accordance with the teachings of the respective patents.

As used herein, lower-alkyl is $C_{1-7}$-alkyl, straight-chained or branched. Lower-alkoxy similarly is $C_{1-7}$-alkoxy.

In the substituent groups $R_1$, $R_2$ and $R_3$ of formula I, the preferred halogen is chlorine, the preferred lower alkyl group is methyl, and the preferred lower alkoxy group is methoxy. In the substituent group $R_4$ of formula II, the preferred lower alkyl groups are methyl and ethyl, with methyl being espeically preferred.

The especially preferred anthranilic acid derivative used in carrying out the method of the invention is a compound of the formula:

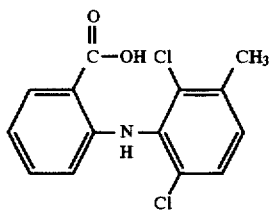

its pharmaceutically acceptable salts and pharmaceutically acceptable esters. The compound of formula Ia encompasses meclofenamic acid and its pharmaceutically acceptable salts and pharmaceutically acceptable lower alkyl esters. The preferred compound of formula Ia is meclofenamate sodium, a non-steroidal anti-inflammatory drug (NSAID) which is approved for analgesic use in osteo- and rheumatoid arthritis, mennorrhagia and dysmenorrhea (Conroy et al., 1991). Meclofenamate sodium is also known to be an inhibitor of lipid catabolism. Hereinafter the term "meclofenamate" shall refer to meclofenamate sodium.

Other preferred anthranilic acid derivatives for carrying out the method of the invention are:

tolfenamic acid which is a compound of formula I having the formula:

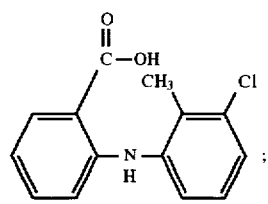

mefanamic acid which is a compound of formula II having the formula:

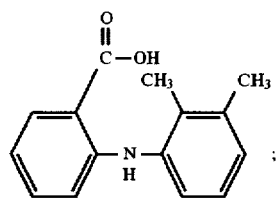

and flufenamic acid which is a compound of fomula III having the formula:

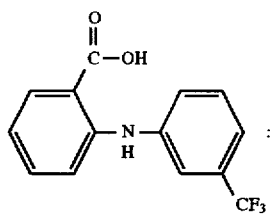

their pharmaceutically acceptable salts and pharmaceutically acceptable esters. Particularly preferred are the salts of the compounds of formulas Ib, IIa and IIIa, especially the sodium salts. Hereinafter, the terms tolfenamate, mefanamate and flufenamate shall refer to the sodium salts of the respective acids.

Treating neurotoxic injury within the meaning of the present invention means reducing the extent of damage to central neurons surrounding a central neuron which has released glutamate due to its having been damaged by a neurotoxic event. Neurotoxic events include acute neurological insults such as hypoxia/ischemia, such as occurs during stroke, hypoglycemia, epilepsy or trauma. Neurotoxic events may also be chronic neuronal damage caused by neurodegenerative disorders such as Huntington's disease, Alzheimer's disease, amyotropic lateral sclerosis, and the neurodegenerative effects of AIDS. Thus, the present invention also comprises a method of treating diseases in which said neurotoxic injury occurs.

The anthranilic acid derivatives described herein inhibit arachidonic acid ("AA") metabolism (Dumuis et al, 1988; Sanfeliu et al., 1990; Rordorf et al., 1991) so that neurotoxic metabolite and oxygen-derived free radical formation is inhibited. The AA is released in neurons due to an influx of excessive $Ca^{2+}$ into the neuronal cells which is caused by NMDA receptor stimulation by glutamate (the glutamate having been released by neurons which were damaged by the neurotoxic event, itself). The excessive $Ca^{2+}$ influx activates phospholipase $A_2$, a calcium-dependent enzyme which breaks down cell membranes liberating the AA. The metabolism of AA by endogenous lipoxygenases and cyclooxygenases leads to the production of the oxygen free radicals that trigger peroxidative degradation of neuronal lipid membranes (Siesjo et al., 1980; Chan et al., 1985) which results in the neuronal damage or death. In addition, the formation of AA metabolites increases ischemia-induced injury, promoting infarct expansion (Chan et al, 1985; Lefer, 1986, Bazan, 1989; Dugan and Choi, 1994). Therefore, in accordance with the present invention, inhibiting AA metabolism inhibits both metabolite and oxygen-derived free radical formation, and provides an alternative mechanism by which glutamate-induced neurotoxicity is inhibited.

A further embodiment of the present invention is a method of inhibiting neurotoxic injury in a patient where said injury is caused by the metabolism of arachidonic acid released by neurons due to stimulation by glutamate of NMDA receptors of said neurons by administering to said patient a composition comprising an anthranilic acid derivative as herein described and a pharmaceutically acceptable carrier in an amount sufficient to inhibit said neurotoxic injury.

The preferred embodiment of the invention comprises a method of treating stroke by administrering to a stroke patient a composition comprising an anthranilic acid derivative as herein described and a pharmaceutically acceptable carrier in an amount sufficient to treat said stroke. In accordance with the present invention, stroke is defined as an acute neurotoxic event in the brain of a patient wherein the neurotoxic event occurs due to a loss of blood flow to neurons of the brain.

The pharmaceutically acceptable cations encompassed by group M in formula I include any cation chemically permissible in the art for said compound and applicable to human patients in a pharmaceutically acceptable preparation. Any such conventional pharmaceutically acceptable cation can be utilized. Among the conventional cations which can be utilized there are the alkali metal cations such as sodium or potassium, alkaline earth metal cations such as calcium or magnesium, and ammonium or amine cations. Additionally, pharmaceutically acceptable lower-alkyl group can be used as group M in formula I.

The anthranilic acid derivatives described herein are administered systemically as a composition containing the active compound and a pharmaceutically acceptable carrier compatible with said compound. In preparing such a composition, any conventional pharmaceutically acceptable carrier can be utilized. When the drug is administered orally, it is generally administered at regular intervals.

In therapeutic use, the method of the invention may be carried out by administering the composition containing the anthranilic acid derivative by any route whereby drugs are conventionally administered. Such routes include intravenously, intramuscularly, subcutaneously, intrathecally, intraperitoneally, as well as orally. Preferably, the method of the invention is carried out via oral or intravenous routes of administration.

The pharmaceutical compositions can be made up in any conventional form, including a solid form for oral administration such as tablets, capsules, pills, powders, granules, and the like. The pharmaceutical compositions may be sterilized and/or may contain adjuvants such as preservatives, stabilizers, wetting agents, emulsifiers, salts for varying the osmotic pressure, and/or buffers.

Typical preparations for intravenous administration would be sterile aqueous solutions including water/buffered solutions. Intraveneous vehicles include fluid, nutrient and electrolyte replenishers. Preservatives and other additives may also be present such as antibiotics and antioxidants. Compositions for bolus i.v. administration may contain up to 10 mg/ml (10,000 mg/liter) of an anthranilic acid derivative described herein. Compositions for drip i.v. administration preferably contain from about 50 mg/liter to about 500 mg/liter of an anthranilic acid derivative described herein.

In accordance with this invention, the anthranilic acid derivatives described herein are useful in pharmaceutically acceptable oral modes. These pharmaceutical compositions contain said compound in association with a compatible pharmaceutically acceptable carrier material. Any conventional carrier material can be utilized. Any conventional oral dosage form such as tablets, capsules, pills, powders, granules, and the like may be used. The carrier material can be an organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutical composition may contain other pharmaceutically active agents. Additional additives such as flavoring agents, preservatives, stabilizers, emulsifying agents, buffers and the like may be added in accordance with accepted practices of pharmaceutical compounding.

A preferred oral dosage form comprises tablets, capsules of hard or soft gelatin, methylcellulose or of another suitable material easily dissolved in the digestive tract. The oral dosages contemplated in accordance with the present invention will vary in accordance with the needs of the individual patient as determined by the prescribing physician. The preferred oral dosage form is capsules or tablets containing from 50 to 500 mg of a compound of the invention.

In carrying out the method of the invention, a compound of the invention is generally given to adults daily, preferably orally or intravenously, in an amount of from about 5 mg/kg to about 30 mg/kg daily, in single or divided doses, preferably from about 13 mg/kg to about 17 mg/kg daily, with the precise dosage being varied depending upon the needs of the patient. In general, this therapy is carried out for a period of about three months. Alternatively, the method of the invention may be carried out prophylactically for an indefinite time in those patients who are have a high risk of suffering an acute neurotoxic event, such as a stroke. For the treatment of an acute neurotoxic event, the patient should be treated in accordance with the method of the invention as soon as possible after the diagnosis of the acute neurotoxic event, preferably within twelve hours, and most preferably within six hours, of the onset of the neurotoxic event.

Examples 1–9, below, demonstrate that the anthranilic acid derivatives described herein limit NMDA receptor-mediated toxicity in cortical cell cultures in vitro as well as in an animal model of cerebral ischemia in vivo.

In particular, the data in Table 2, below, demonstrates that meclofenamate sodium has a powerful protective effect against NMDA receptor-mediated neurotoxicity. The data in Table 2 also demonstrates that many other non-anthranilic acid derived lipid catabolism inhibitors do not provide any large protective effects like those seen with meclofenamate. Thus meclofenamate is distinguishable from other lipid catabolism inhibitors, perhaps because it possesses a special balance of inhibitory effects on both lipoxygenase and cyclooxygenase pathways.

Experimental Procedures

Cell Culture: Mixed cortical cultures containing both neuronal and glial elements were prepared from fetal mice at 15 day gestation as previously described (Hewett et al., 1993). Glia were plated in Primaria (Falcon) 15 mm multiwell vessels in modified Eagle's medium (MEM, Earle's salts), with 2 mM glutamine, 25 mM glucose, 10% fetal bovine serum, 10% horse serum, and 10 ng/ml epidermal growth factor. Dissociated cortical cells were plated (2.75 hemispheres/10 ml/plate) in a similar medium (with only 5% fetal bovine serum and 5% horse serum) on an established bed of glia (15–30 days in vitro). All cultures were kept at 37° C. in a humidified 5% $CO_2$-containing atmosphere. After 3–7 days in vitro, glial cell division was halted by 2 days of exposure to 10 μM cytosine arabinoside. Cells were subsequently shifted into maintenance medium which was identical to the plating medium, but lacked fetal bovine serum. The medium was changed twice weekly. Experiments were performed on cortical cultures after 14 days in vitro.

Drug Exposure: Cells were exposed to NMDA for 5 min either alone or in the presence of test compound at room temperature in a HEPES controlled salt solution (HCSS), containing (mM): NaCl, 120; KCl, 5.4; $MgCl_2$, 0.8; $CaCl_2$, 1.8; HEPES, 20; glucose, 15, and glycine, 0.01 (pH 7.4). The exposure solution was then washed away and replaced by MEM (Earle's salts) supplemented with glycine (0.01 mM) and the cells returned to the incubator for 20–24 hr.

Since the neurotoxicity of NMDA preparations can vary from lot to lot, the concentration of NMDA used was determined empirically in a separate benchmarking test. Cells were exposed as described above to increasing concentrations of NMDA, and neuronal injury is assessed as described below. A dose/response curve is plotted, and a concentration which induces death in 50–70% of the neuronal population after 24 hours is used as the test concentration for evaluating compounds as neuroprotective drugs. Typical NMDA concentrations which have been found to induce death in 50–70% of the neuronal population are in the range of 100–400 μM.

Assessment of Neuronal Cell Injury: Neuronal cell death was estimated by examination of cultures under phase-contrast microscopy, and quantified by measurement of lactate dehydrogenase (LDH) released by damaged or destroyed cells into the bathing medium one day following experimentation (Koh, J. Y. and Choi, D. W., 1987). The LDH signal corresponding to near-complete neuronal death was determined by assaying the supernatant of sister cultures which were exposed to 500 μM NMDA for 24 hr in MEM supplemented with 10 μM glycine. Background LDH levels (generally <15% of total neuronal) were determined in sister cultures subjected to sham wash and subtracted from the levels in experimental conditions to yield the LDH signal specific to experimental injury.

EXAMPLE 1

Effect of meclomenamate sodium on NMDA-mediated excitotoxicity

Mouse cortical cultures were exposed for 5 min to NMDA (100 μM) alone or in the presence of increasing concentrations of meclofenamate sodium, as described under Experimental Procedures, above. The results are shown in FIG. 1. Values represent the mean LDH±SEM (n=5–7) scaled to the mean LDH found in control injury (=100). An asterisk indicates a value significantly different from control as determined by analysis of variance followed by Dunnett's t-test for multiple comparison (p<0.01).

EXAMPLE 2

Concentration-response curve of NMDA in the presence and absence of meclofenamate.

Figure 2:
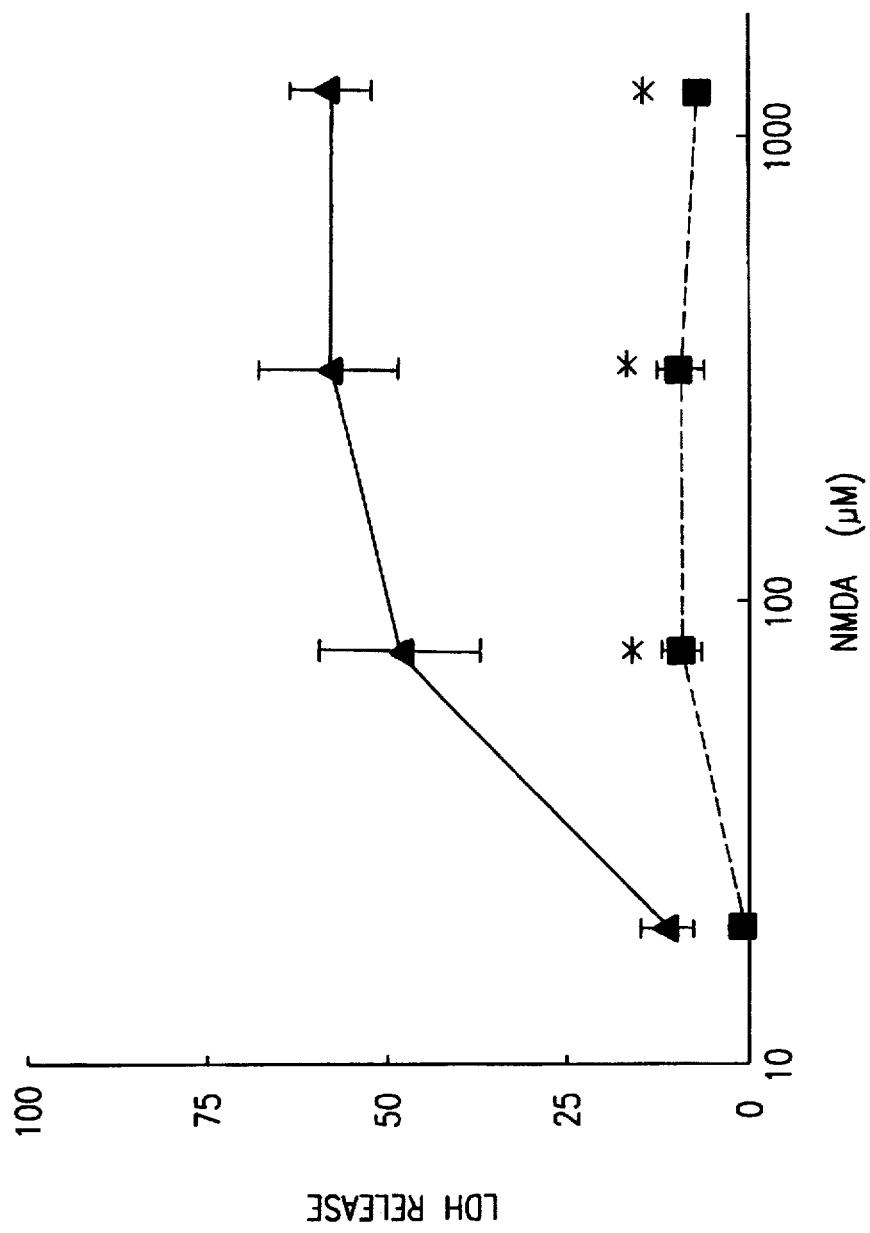
FIG. 2. Concentration-response curve of NMDA in the presence and absence of meclofenamate (300 μM).

Mouse cortical cultures were exposed, as described in Example 1, for 5 min to solutions containing increasing concentrations of NMDA or NMDA plus 300 μM meclofenamate. LDH activity was assessed 20–24 hr later. Data are expressed as the percentage of total LDH released (mean ±SEM; n=10). Total LDH was determined by assaying the supernatant of sister cultures which were incubated with 500 μM NMDA for 24 hr. The results are shown in FIG. 2. An asterisk indicates difference form untreated controls as determined by repeated measures Analysis of Variance ("ANOVA") followed by Bonferroni's t-test for multiple comparisons (p<0.01).

EXAMPLE 3

Effect of meclofenamate on NMDA Current

Electrophysiological Recording: NMDA current was recorded at room temperature (25° C.) from DIV 12–20 cortical neurons plated on 35 mm dishes using whole-cell recording (EPC-7, List-Electronic, Germany) under voltage clamp. The data acquisition program, PULSE (HEKA Electronic, Germany), was used to control the voltage clamp, to monitor and to collect current and voltage data on a Macintosh computer (Quatra 950, Apple Computer Corp., USA). The extracellular solution contained (mM): NaCl, 145; KCl, 3; $MnCl_2$, 2; $CaCl_2$, 2; glycine, 0.01; HEPES, 10; TTX, 0.005 and glucose, 5. The recording electrode's internal solution contained (mM) CsCl, 150, ATP-Na, 2, BAPTA, 0.5 and HEPES, 10. All solutions were adjusted to pH 7.3 by Tris buffer. NMDA (100 μM) in the extracellular solution was delivered to the cell by a multi-channel DAD drug delivery system (Adams and List Inc., New York.) To eliminate dilution of drug, meclofenamate was added to the bath medium and NMDA was delivered in an extracellular solution containing the same concentration of drug.

Figure 3:
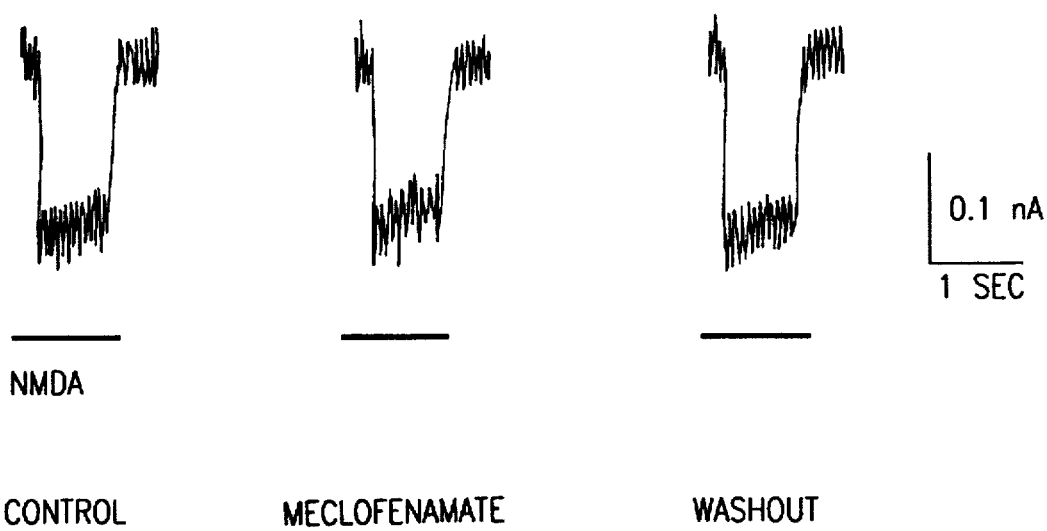
FIG. 3 Effect of meclofenamate on NMDA current.

Ten min prior to NMDA (100 μM) application, mouse cortical cells were treated with 300 μM meclofenamate. NMDA current was recorded using whole cell recording techniques. To eliminate dilution of drug, NMDA was delivered to the cell in a solution containing the same concentration of drug as that in the bath. Results are shown in FIG. 3.

EXAMPLE 4

Effect of meclofenamate on $^{45}Ca^{2+}$ accumulation during NMDA exposure.

$^{45}Ca^{2+}$ accumulation: Mouse cortical cultures were washed with HCSS and then exposed to NMDA (300 μM) alone or in the presence of increasing concentrations of meclofenamate in HCSS containing a trace amount of $^{45}Ca^{2+}$ (0.5 μCi/well; NEN, Boston, Mass.). After 5 min the exposure solution was washed out with four rinses of HCSS (750 μl each) and the cells were lysed by addition of 0.2% sodium dodecyl sulfate (SDS) at 37° C. An aliquot of cell lysate was estimated by β-counting.

Figure 4:
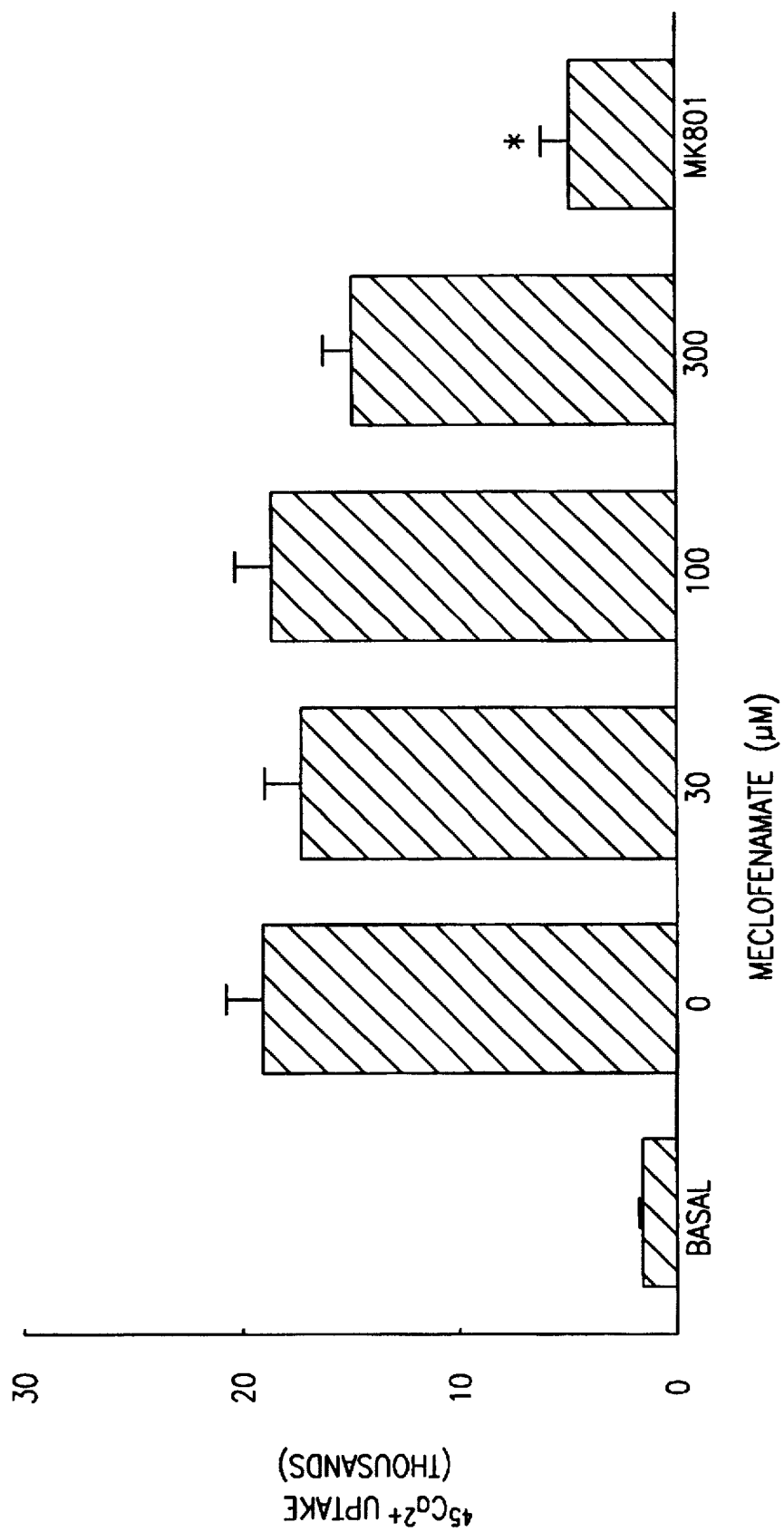
FIG. 4. Effect of meclofenamate on $^{45}Ca^{2+}$ accumulation during NMDA exposure.

Mouse cortical cultures were exposed, as in Example 1, for 5 min to NMDA (300 μM) alone or NMDA plus increasing concentrations of meclofenamate in the presence of extracellular $^{45}Ca^{2+}$. Results are shown in FIG. 4. Values are expressed as mean ±SEM (n=18). Meclofenamate did not significantly affect uptake at any concentration tested, as determined by Kruskal-Wallis ANOVA.

EXAMPLE 5

Effect of meclofenamate on KCl-stimulated Influx of Calcium.

Cytosolic Calcium Measurements: Intracellular free calcium was measured using fura-2 fluorescence videomicroscopy. Mixed neuronal/glial cultures plated in glass-coverslip-bottomed 35 mm dishes were loaded with fura-2 by incubation (30 min, 25° C.) in 5 μM fura-2AM in HCSS plus 0.1% PLURONIC F-127. Cultures were then washed twice with HCSS and incubated for an additional 30 min to allow for hydrolysis of the ester. Experiments were performed on cells between days 12 and 17 in vitro at room temperature, under constant perfusion with HCSS (perfusion rate 1–2 ml/min) on the stage of a Nikon DIAPHOT inverted microscope equipped with a 75 W xenon lamp and a Nikon 40X, 1.3 N.A. epifluorescence oil immersion objective. Light was passed through 340 nm and 380 nm band pass filters mounted on a filter wheel with a computer controlled shutter. The light was then reflected off a dichroic mirror (400 nm) and passed through a 470–550 nm emission filter. Images were acquired with a CCD camera (Quantex) and digitized (256×512 pixels) using the Image-1 system (Universal Imaging). Background fluorescence was measured from a cell free region of the coverslip at the end of each experiment and subtracted from each 340 and 380 image. All drugs were delivered through the perfusion system.

Figure 5:
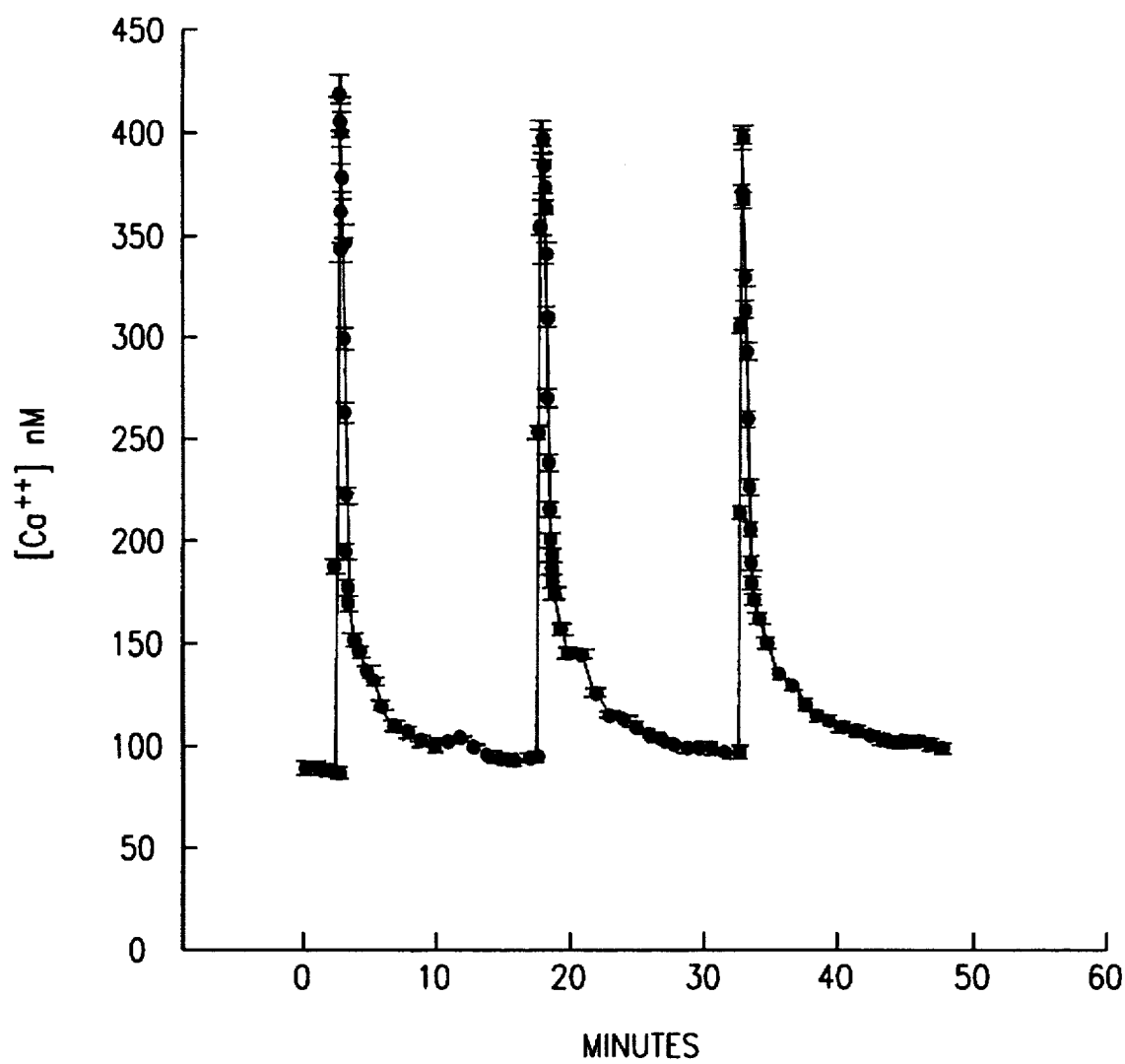
FIG. 5. Effect of meclofenamate on KCl-stimulated influx of calcium.

Cells were exposed for 5 minutes, as in Example 1, to 60 mM KCl in the presence and absence of meclofenamate (300 μM). Intracellular free calcium [Ca$^{2+}$]i was measured using fura-2 fluorescence videomicroscopy. Results are shown in FIG. 5.

EXAMPLE 6

Neuroprotective Effect of Meclofenamate in Induced Focal Cerebral Ischemia

Surgical MCAO occlusion: Focal cerebral ischemia, confined to the cerebral cortex in the right middle cerebral artery territory (MCA) of Long Evans male rats (250–350 g; Charles Rivers, Wilmington, Del.), was induced by temporary ligation of the MCA and both common carotid arteries (CCAs) as described by Chen et al., 1986. The rectal temperature was monitored and maintained at 37.0°±0.5° C. via an electronic temperature controller (Versa-Therm 2156, Cole-Parmer, Chicago, Ill.) linked to a heating lamp. Physiological parameters including plasma blood glucose, arterial blood pressure, and pulse rate were monitored as described previously and maintained within normal range (Liu et al, 1989). Reperfusion was initiated by releasing arterial occlusion affecting all 3 vessels after 90 min of ischemia. Restoration of blood flow in all three arteries was observed directly under the microscope. Rats were treated i.p. with vehicle (control) or meclofenamate (10 mg/kg, i.p.) 15 min before ischemia.. The cortical infarct volume was morphometrically measured after triphenyl tetrazolium chloride stain 24 hr after MCAO.

31 rats underwent middle cerebral artery occlusion (MCAO) followed by reperfusion. Fourteen rats underwent MCAO alone while 17 rats were given intraperitoneal meclofenamate (10 mg/kg) 15 minutes prior to 90 min MCAO. Meclofenamate reduced infarct volume from 144.8±8.8 mm$^3$ in control animals to 99.2±9.2 in treated animals (significantly different at p<0.002).

Discussion:

Meclofenamate given at the same time as NMDA, dose-dependently decreased neuronal injury as assessed by a reduction in the amount of lactate dehydrogenase released into the extracellular fluid (FIG. 1). Complete neuroprotection by meclofenamate (300 μM) was observed over a full concentration-toxicity curve for NMDA (FIG. 2).

Electrophysiological and radiotracer flux measurements determined that meclofenamate was not an NMDA receptor antagonist. Meclofenamate at 300 μM, a concentration that was completely neuroprotective, failed to alter the current elicited by application of NMDA (FIG. 3). Likewise, NMDA-induced $^{45}Ca^{2+}$ influx was not significantly altered by concurrent application of meclofenamate (FIG. 4).

Finally, meclofenamate sodium had no effect on the elevation of intracellular calcium produced by KCl stimulation indicating that it does not block voltage-gated calcium channels in our cultures.(FIG. 5). RIA measurements of lipid breakdown products following NMDA exposure indicated that meclofenamate was able to block formation of both cyclooxygenase and lipoxygenase metabolites, a finding consistent with the conclusion of prior studies suggesting that this compound is a dual lipoxygenase/cyclooxygenase inhibitor (data not shown).

The data discussed above demonstrates that meclofenamate sodium is neuroprotective both in an in vitro model of excitotoxicity and in an in vivo model of cerebral ischemia. Most likely, meclofenamate exerts its neuroprotective effects by acting subsequent to NMDA receptor activation, and inhibiting both neuronal cell cyclooxygenase activity and neuronal cell lipoxygenase activity; other effects may also contribute. We propose that meclofenamate, or related chemical compounds, may have therapeutic use in human neurological diseases linked to excessive glutamate receptor stimulation, especially that mediated by NMDA receptors.

TABLE 2

Effect of inhibitors of arachidonic acid metabolism on NMDA-induced neurotoxicity.

|  | % of control | n |
|---|---|---|
| Cyclooxygenase inhib |  |  |
| naproxen (300 μM) | 82.5 ± 7.1 | 6 |
| ibuprofen (100 μM) | 65.4 ± 3.5* | 6 |
| Lipooxygenase inhib |  |  |
| ETYA (300 μM) | 85.1 ± 6.2 | 8–9 |
| Esculetin (300 μM) | 116.6 ± 17.1 | 6 |
| NDGA (30 μM) | 101 ± 11.0 | 30 |
| ETI (300 μM) | 107 ± 13.0 | 4 |
| Dual CO/LO inhib |  |  |
| Meclofenamate (300 μM) | 10.8 ± 5.1* | 5–7 |
| Phenidone (300 μM) | 58.1 ± 6.7* | 21 |

Cells were exposed to NMDA (100–200 μM) (as described previously) both in the presence and absence of cyclooxygenase/lipooxygenase inhibitors. Data represents the mean LDH±SEM scaled to the mean LDH found in control injury (NMDA alone=100). Data were analyzed via ANOVA followed by Dunnett's t-test for multiple comparisons. An asterisk indicates a value significantly different from control.

EXAMPLE 7

Effect of tolfenamate sodium on NMDA-mediated Excitotoxicity

Figure 6:
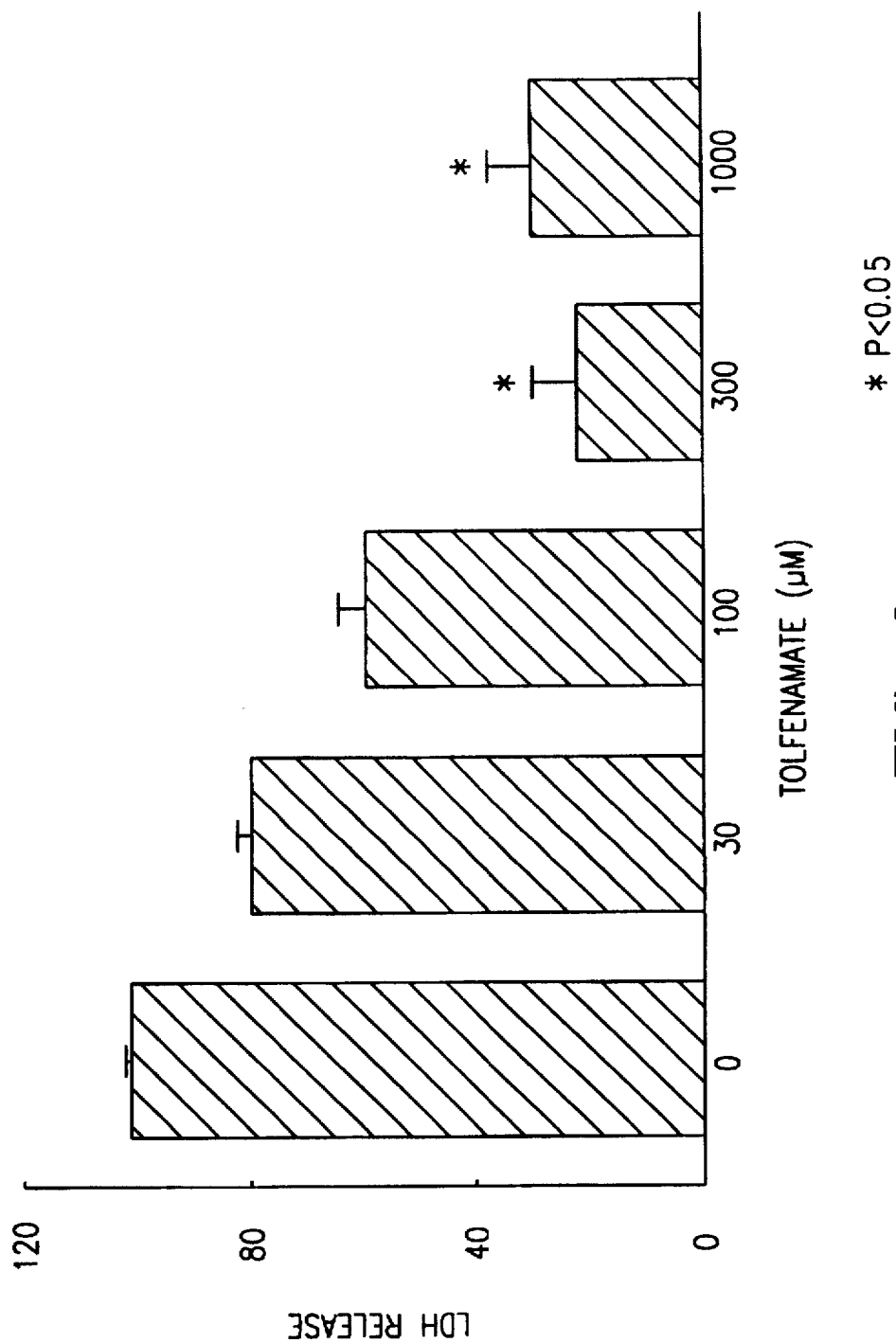
FIG. 6. Effect of tolfenamate sodium on NMDA-mediated excitotoxicity.

Mouse cortical cultures were exposed for 5 minutes to NMDA (400 μM) alone or in the presence of increasing concentrations of tolfenamate sodium, as described under Experimental Procedures, above. The results are shown in FIG. 6. Values represent the mean LDH±SEM (n=6–7)

scaled to the mean LDH found in control injury (=100). An asterisk indicates a value significantly different from control as determined by analysis of variance followed by Dunnett's t-test for multiple comparison (p<0.05).

EXAMPLE 8

Effect of mefenamate sodium on NMDA-mediated excitotoxicity

Figure 7:
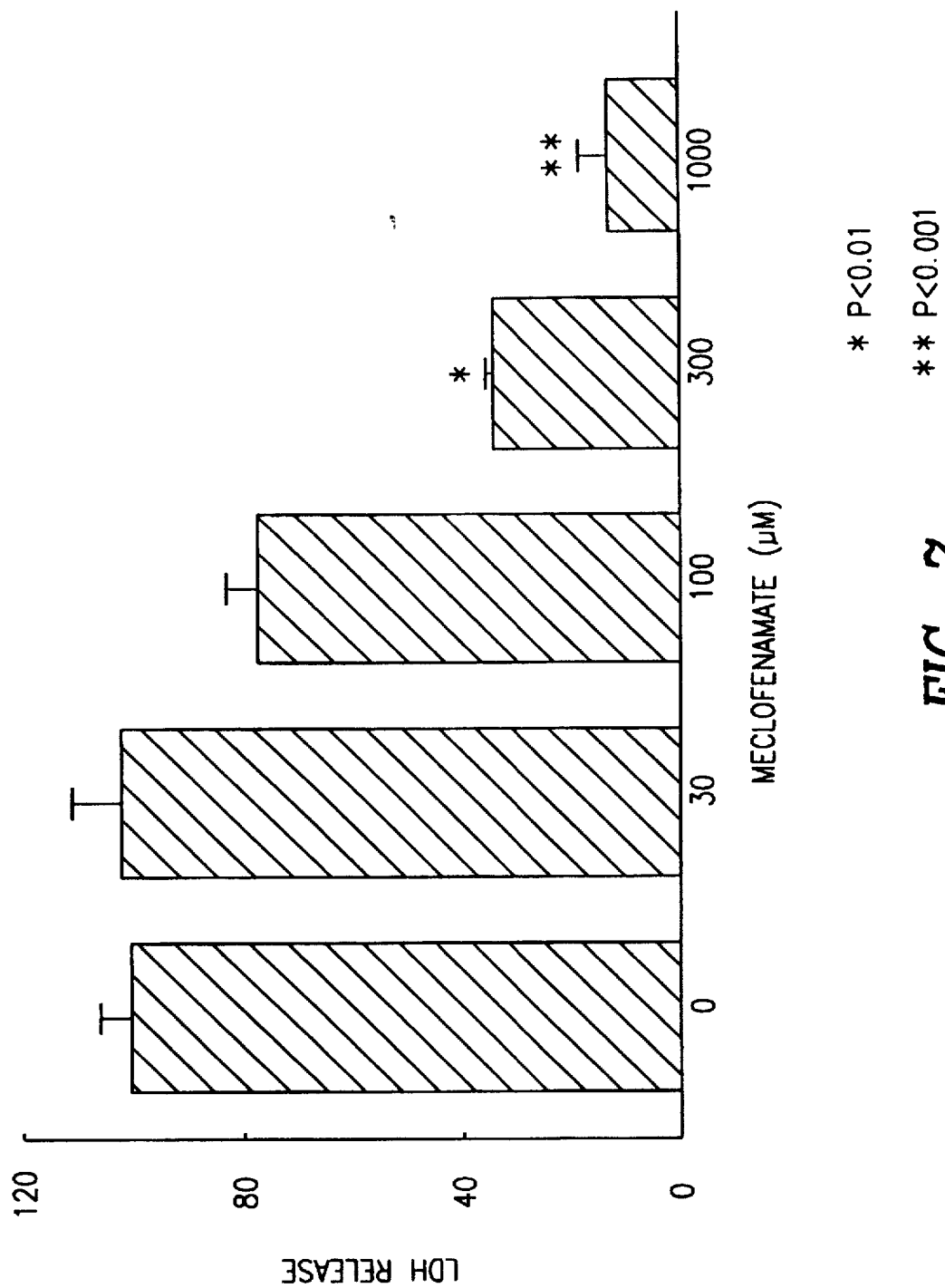
FIG. 7. Effect of mefenamate sodium on NMDA-mediated excitotoxicity.

Mouse cortical cultures were exposed for 5 minutes to NMDA (400 μM) alone or in the presence of increasing concentrations of mefenamate sodium, as described under Experimental Procedures, above. The results are shown in FIG. 7. Values represent the mean LDH±SEM (n=6–7) scaled to the mean LDH found in control injury (=100). An asterisk indicates a value significantly different from control as determined by analysis of variance followed by Dunnett's t-test for multiple comparison (p<0.01).

EXAMPLE 9

Effect of flufenamate sodium on NMDA-mediated Excitotoxicity

Figure 8:
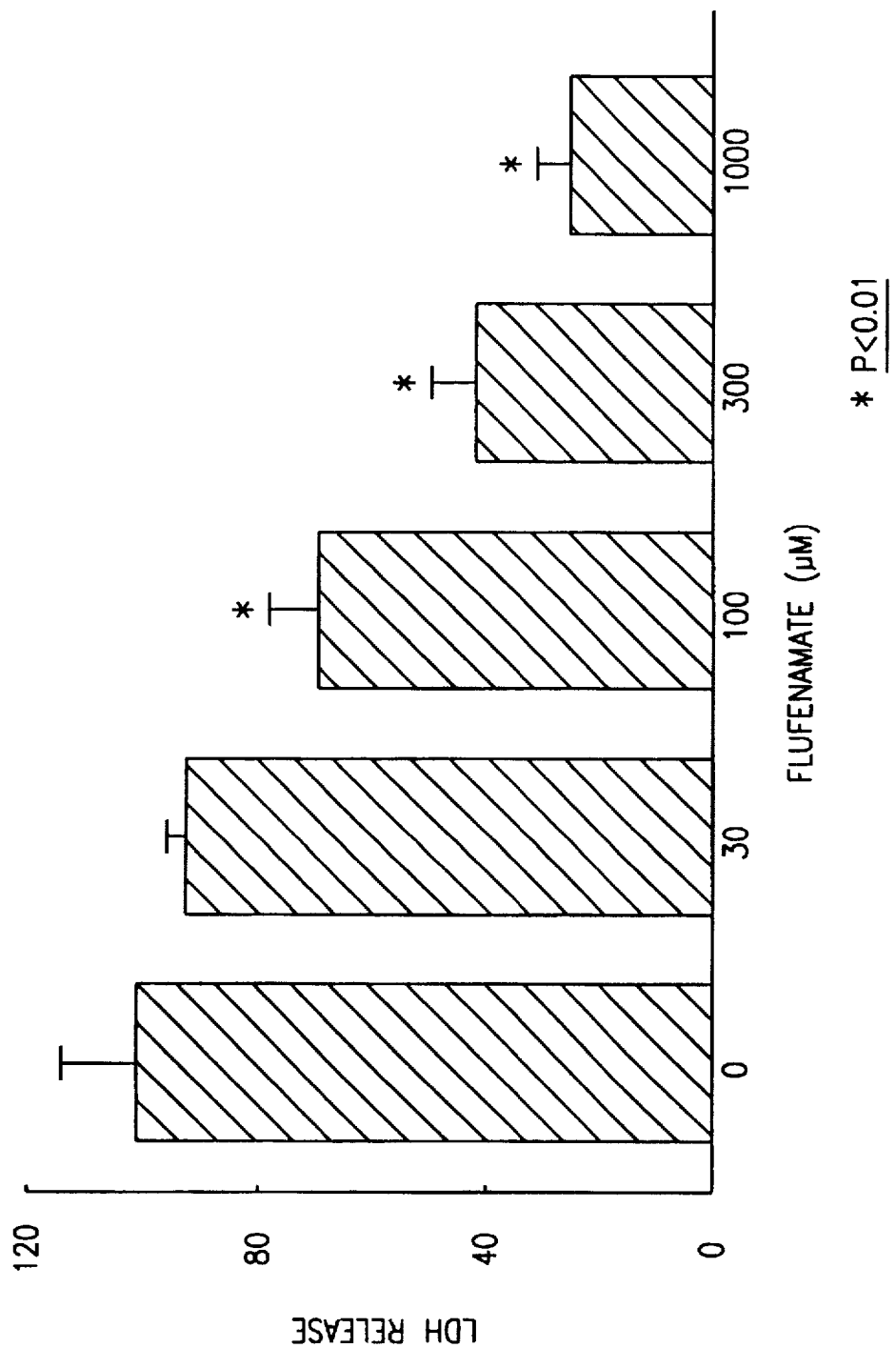
FIG. 8. Effect of flufenamate sodium on NMDA-mediated excitotoxicity.

Mouse cortical cultures were exposed for 5 minutes to NMDA (400 μM) alone or in the presence of increasing concentrations of flufenamate sodium, as described under Experimental Procedures, above. The results are shown in FIG. 8. Values represent the mean LDH±SEM (n=6–8) scaled to the mean LDH found in control injury (=100). An asterisk indicates a value significantly different from control as determined by analysis of variance followed by Dunnett's t-test for multiple comparison (p<0.01).

REFERENCES

Bazan, N. G. (1989) Arachidonic acid in the modulation of excitable membrane function and at the onset of brain damage. In: Arachidonic acid metabolism in the nervous system. Physiological and pathophysiological significance (Barkai, A. L, Bazan, N. G., eds) p 1. New York: N.Y. Acad. Sci.

Chan, P. H., Fishman, R. A., Longar, S. Chen, S., Yu, A. (1985) Cellular and molecular effects of polyunsaturated fatty acids in brain ischemia and injury. Prog. Brain Res. 63: 227–235.

Chen ST, Hsu CY, Hogan EL, Macriq H, Balentine JD (1986): A model of focal ischemic stroke in the rat: reproducible extensive cortical infarction. Stroke 17: 738–743.

Choi, D. W. (1988) Glutamate toxicity and diseases of the nervous sytem. Neuron 1: 623–634.

Choi, D. W. (1990) Methods for antagonizing glutamate neurotoxicity. Cerebrovasc. Brain Metab. Rev 2: 105–147.

Choi, D. W. (1991) "Excitotoxicity:. In: Excitatory amino acid antagonists. B. S. Meldrum, Ed. Blackwell Scientific Publications, London, pp. 216–236.

Conroy, M. C., Randinitis, E. J., Turner, J. L. (1991) Pharmacology, pharmacokinetics and therapeutic use of meclofenamate sodium. Clin. J. Pain. 7 Suppl 1: S44–8.

Coyle, J. T., Bird, S. J., Evans, R. H., Gulley, R. L., Nadler, J. V., Nicklas, W. J., Olney, J. W. (1981) Excitatory amino acid neurotoxins: selectivity and mechanisms of action. Neurosci. Res. Prog. Bulletin 19: 3331–427.

Dugan, L. L., Choi, D. W. (1994) Excitotoxicity, free radicals and cell membrane changes. Ann. Neurol. 35: S17–21.

Dumuis, A., Sebben, M., Haynes, L., Pin, J.-P., Bockaert, J. (1988) NMDA receptors activate the arachidonic acid cascade in striatal neurons. Nature 336: 68–70.

Goldberg, M. P., Weiss, J. W., Pham, P. C., Choi, D. W. (1987) J. Pharmacol. Exp. Ther. 243: 784–791.

Halliwell, B., Gutteridge, J. M. C. (1985) Oxygen radicals and the nervous sytem. Trends Neurosci. 8: 22–26.

Hewett, S. J., Corbett, J. A., McDaniel, M. L., Choi, D. W. (1993) Inhibition of nitric oxide formation does not protect murine cortical cell cultures from N-methyl-D-aspartate toxicity. Brain Res. 625: 337–341.

Koh, J. Y. and Choi, D. W. (1987) Quantitative determination of glutamate- mediated cortical neuronal injury in cell culture by lactate dehydrogenase efflux assay. J. Neurosci. Methods 20: 83–90.

Lefer, A. M. (1986) Leukotrienes as mediators of ischemia and shock. Biochem. Pharmacol. 35: 123–127.

Lipton, S. A. (1992) Models of neuronal injury in AIDS: another role for the NMDA receptor? Trends Neurosci. 15: 75–9.

Liu TH, Beckman JS, Freeman BA, Hogan EL, Hsu CY (1989): Polyethelene glycol-conjugated superoxide dismutase and catalase reduce ischemic brain injury. Am J Physiol 256: H589–593.

Meldrum, B. (1985) Possible therapeutic applications of antagonists of excitatory amino acid transmitters. Clin. Sci. 68: 113–122.

Meldrum. B., Garthwaite, J. (1990) Excitatory amino acid neurotoxicity and neurodegenerative disease. Trends Pharmacol. Sci. 11: 379–387.

Olney, J. W. (1986) Inciting excitotoxic cytocide among central neurons. Adv. Exp. Med. Biol. 203: 631:645.

Rordorf, G. Uemura, Y., Boneventre, J. V. (1991) Characterization of phospholipase $A_2$ ($PLA_2$) activity in gerbil brain: enhanced activities of cytosolic, mitochondrial , nd microsomal forms after ischemia and reperfusion. J. Neurosci. 11: 1829–1836.

Rothman, S. M., Olney, J. W. (1987) Excitotoxicity and the NMDA receptor. Trends Neurosci. 10: 299–302.

Sanfelieu, C., Hunt, A., Patel, J. (1990) Exposure to N-methyl-D-aspartate increases release of arachidonic acid in primary cultures of rat hippocampal neurons and not in astrocytes. Brain Res. 526: 241–248.

Siesjo, B. K., Rehncrona, S., Smith, D. (1980) Neuronal cell damage in the brain: possible invovement of oxidative mechanisms. Acta Physiol. Scand. [Suppl] 492: 121–128.

We claim:

1. A method of treating neurotoxic injury in a patient suffering from said injury by administering to said patient a composition comprising an anthranilic acid derivative selected from the group consisting of:

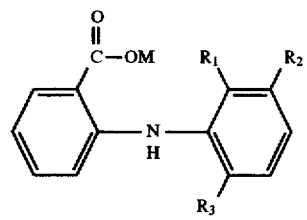

wherein $R_1$ is halogen or methyl; $R_2$ is halogen, lower alkyl, lower alkoxy, benzyloxy or β,β,β-trifluoroethoxy wherein at least one of $R_1$ and $R_2$ are halogen; $R_3$ is hydrogen, halogen or methyl; M is hydrogen, a pharmaceutically acceptable cation or lower-alkyl;

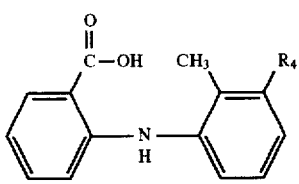

wherein $R_4$ is lower alkyl; and

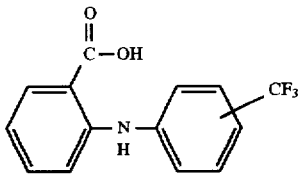

their pharmaceutically acceptable salts and pharmaceutically acceptable esters, and a pharmaceutically acceptable carrier, wherein said anthranilic acid derivative is present in said composition in an amount sufficient to treat said neurotoxic injury.

2. The method of claim 1 wherein said anthranilic acid derivative is a compound of the formula:

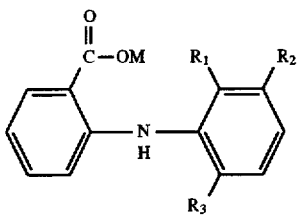

wherein $R_1$ is halogen or methyl; $R_2$ is halogen, lower alkyl, lower alkoxy, benzyloxy or $\beta,\beta,\beta$-trifluoroethoxy wherein at least one of $R_1$ and $R_2$ are halogen; $R_3$ is hydrogen, halogen or methyl; M is hydrogen, a pharmaceutically acceptable cation or lower-alkyl.

3. The method of claim 2 wherein said anthranilic acid derivative is meclofenamate sodium.

4. The method of claim 3 wherein said anthranilic acid derivative is administered in an amount from about 5 mg/kg to about 30 mg/kg daily.

5. The method of claim 4 wherein said anthranilic acid derivative is administered in an amount from about 13 mg/kg to about 17 mg/kg daily.

6. The method of claim 5 wherein said anthranilic acid derivative is administered orally.

7. The method of claim 5 wherein said anthranilic acid derivative is administered intravenously.

8. The method of claim 2 wherein said anthranilic acid derivative is tolfenamate sodium.

9. The method of claim 8 wherein said anthranilic acid derivative is administered in an amount from about 5 mg/kg to about 30 mg/kg daily.

10. The method of claim 9 wherein said anthranilic acid derivative is administered in an amount from about 13 mg/kg to about 17 mg/kg daily.

11. The method of claim 10 wherein said anthranilic acid derivative is administered orally.

12. The method of claim 10 wherein said anthranilic acid derivative is administered intravenously.

13. The method of claim 1 wherein said anthranilic acid derivative is a compound of the formula:

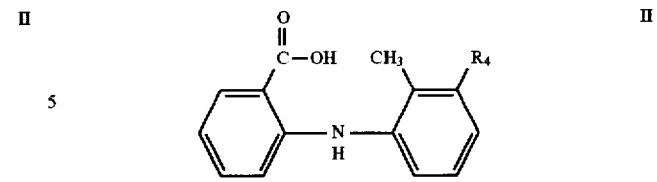

wherein $R_4$ is lower alkyl.

14. The method of claim 13 wherein said anthranilic acid derivative is mefenamate sodium.

15. The method of claim 14 wherein said anthranilic acid derivative is administered in an amount from about 5 mg/kg to about 30 mg/kg daily.

16. The method of claim 15 wherein said anthranilic acid derivative is administered in an amount from about 13 mg/kg to about 17 mg/kg daily.

17. The method of claim 16 wherein said anthranilic acid derivative is administered orally.

18. The method of claim 16 wherein said anthranilic acid derivative is administered intravenously.

19. The method of claim 1 wherein said anthranilic acid derivative is a compound of the formula:

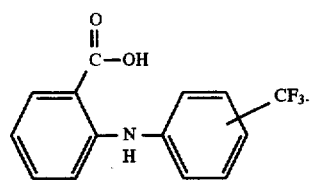

20. The method of claim 19 wherein said anthranilic acid derivative is flufenamate sodium.

21. The method of claim 20 wherein said anthranilic acid derivative is administered in an amount from about 5 mg/kg to about 30 mg/kg daily.

22. The method of claim 21 wherein said anthranilic acid derivative is administered in an amount from about 13 mg/kg to about 17 mg/kg daily.

23. The method of claim 22 wherein said anthranilic acid derivative is administered orally.

24. The method of claim 22 wherein said anthranilic acid derivative is administered intravenously.

25. A method of treating stroke in a patient suffering from said stroke by administering to said patient a composition comprising an anthranilic acid derivative selected from the group consisting of:

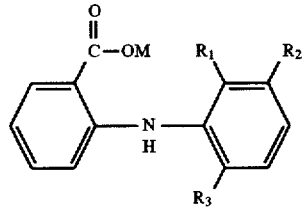

wherein $R_1$ is halogen or methyl; $R_2$ is halogen, lower alkyl, lower alkoxy, benzyloxy or $\beta,\beta,\beta$-trifluoroethoxy wherein at least one of $R_1$ and $R_2$ are halogen; $R_3$ is hydrogen, halogen or methyl; M is hydrogen, a pharmaceutically acceptable cation or lower-alkyl;

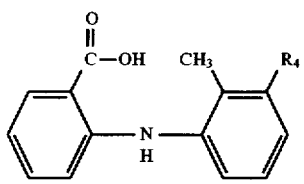

wherein $R_4$ is lower alkyl; and

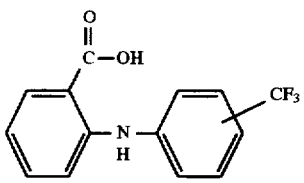

their pharmaceutically acceptable salts and pharmaceutically acceptable esters,
and a pharmaceutically acceptable carrier, wherein said anthranilic acid derivative is present in said composition in an amount sufficient to treat said stroke.

26. The method of claim 25 wherein said anthranilic acid derivative is a compound of the formula:

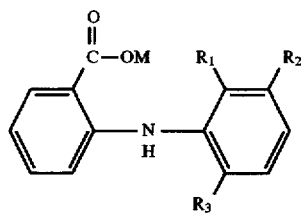

wherein $R_1$ is halogen or methyl; $R_2$ is halogen, lower alkyl, lower alkoxy, benzyloxy or $\beta,\beta,\beta$-trifluoroethoxy wherein at least one of $R_1$ and $R_2$ are halogen; $R_3$ is hydrogen, halogen or methyl; M is hydrogen, a pharmaceutically acceptable cation or lower-alkyl.

27. The method of claim 26 wherein said anthranilic acid derivative is meclofenamate sodium.

28. The method of claim 27 wherein said anthranilic acid derivative is administered in an amount from about 5 mg/kg to about 30 mg/kg daily.

29. The method of claim 28 wherein said anthranilic acid derivative is administered in an amount from about 13 mg/kg to about 17 mg/kg daily.

30. The method of claim 29 wherein said anthranilic acid derivative is administered orally.

31. The method of claim 29 wherein said anthranilic acid derivative is administered intravenously.

32. The method of claim 25 wherein said anthranilic acid derivative is a compound of the formula:

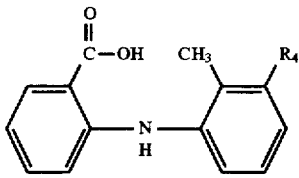

wherein $R_4$ is lower alkyl.

33. The method of claim 32 wherein said anthranilic acid derivative is mefenamate sodium.

34. The method of claim 33 wherein said anthranilic acid derivative is administered in an amount from about 5 mg/kg to about 30 mg/kg daily.

35. The method of claim 34 wherein said anthranilic acid derivative is administered in an amount from about 13 mg/kg to about 17 mg/kg daily.

36. The method of claim 35 wherein said anthranilic acid derivative is administered orally.

37. The method of claim 35 wherein said anthranilic acid derivative is administered intravenously.

38. The method of claim 25 wherein said anthranilic acid derivative is a compound of the formula:

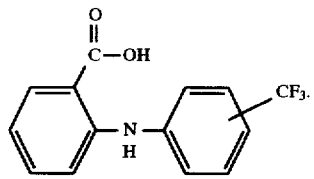

39. The method of claim 38 wherein said anthranilic acid derivative is flufenamate sodium.

40. The method of claim 39 wherein said anthranilic acid derivative is administered in an amount from about 5 mg/kg to about 30 mg/kg daily.

41. The method of claim 40 wherein said anthranilic acid derivative is administered in an amount from about 13 mg/kg to about 17 mg/kg daily.

42. The method of claim 41 wherein said anthranilic acid derivative is administered orally.

43. The method of claim 41 wherein said anthranilic acid derivative is administered intravenously.

44. A method of inhibiting neurotoxic injury in a patient where said injury is caused by the metabolism of arachidonic acid released by neurons due to stimulation by glutamate of NMDA receptors of said neurons by administering to said patient a composition comprising an anthranilic acid derivative selected from the group consisting of:

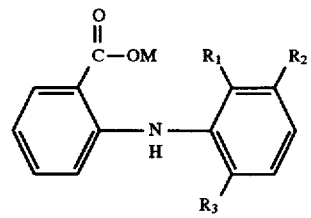

wherein $R_1$ is halogen or methyl; $R_2$ is halogen, lower alkyl, lower alkoxy, benzyloxy or $\beta,\beta,\beta$-trifluoroethoxy wherein at least one of $R_1$ and $R_2$ are halogen; $R_3$ is hydrogen, halogen or methyl; M is hydrogen, a pharmaceutically acceptable cation or lower-alkyl;

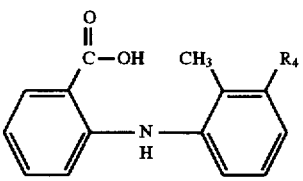

wherein $R_4$ is lower alkyl; and

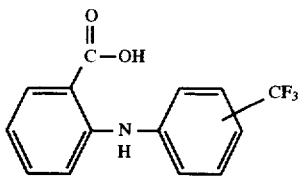

their pharmaceutically acceptable salts and pharmaceutically acceptable esters,
and a pharmaceutically acceptable carrier, wherein said anthranilic acid derivative is present in said composition in an amount sufficient to inhibit said neurotoxic injury.

45. The method of claim 44 wherein said anthranilic acid derivative is a compound of the formula:

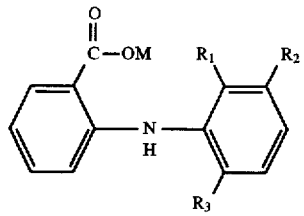

wherein $R_1$ is halogen or methyl; $R_2$ is halogen, lower alkyl, lower alkoxy, benzyloxy or β,β,β-trifluoroethoxy wherein at least one of $R_1$ and $R_2$ are halogen; $R_3$ is hydrogen, halogen or methyl; M is hydrogen, a pharmaceutically acceptable cation or lower-alkyl.

46. The method of claim 45 wherein said anthranilic acid derivative is meclofenamate sodium.

47. The method of claim 46 wherein said anthranilic acid derivative is administered in an amount from about 5 mg/kg to about 30 mg/kg daily.

48. The method of claim 47 wherein said anthranilic acid derivative is administered in an amount from about 13 mg/kg to about 17 mg/kg daily.

49. The method of claim 48 wherein said anthranilic acid derivative is administered orally.

50. The method of claim 48 wherein said anthranilic acid derivative is administered intravenously.

51. The method of claim 45 wherein said anthranilic acid derivative is tolfenamate sodium.

52. The method of claim 51 wherein said anthranilic acid derivative is administered in an amount from about 5 mg/kg to about 30 mg/kg daily.

53. The method of claim 52 wherein said anthranilic acid derivative is administered in an amount from about 13 mg/kg to about 17 mg/kg daily.

54. The method of claim 53 wherein said anthranilic acid derivative is administered orally.

55. The method of claim 53 wherein said anthranilic acid derivative is administered intravenously.

56. The method of claim 44 wherein said anthranilic acid derivative is a compound of the formula:

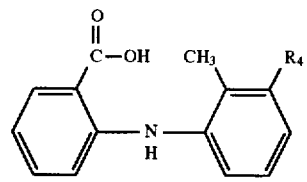

wherein $R_4$ is lower alkyl.

57. The method of claim 56 wherein said anthranilic acid derivative is mefenamate sodium.

58. The method of claim 57 wherein said anthranilic acid derivative is administered in an amount from about 5 mg/kg to about 30 mg/kg daily.

59. The method of claim 58 wherein said anthranilic acid derivative is administered in an amount from about 13 mg/kg to about 17 mg/kg daily.

60. The method of claim 59 wherein said anthranilic acid derivative is administered orally.

61. The method of claim 59 wherein said anthranilic acid derivative is administered intravenously.

62. The method of claim 44 wherein said anthranilic acid derivative is a compound of the formula:

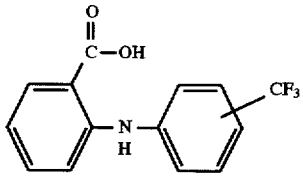

63. The method of claim 62 wherein said anthranilic acid derivative is flufenamate sodium.

64. The method of claim 63 wherein said anthranilic acid derivative is administered in an amount from about 5 mg/kg to about 30 mg/kg daily.

65. The method of claim 64 wherein said anthranilic acid derivative is administered in an amount from about 13 mg/kg to about 17 mg/kg daily.

66. The method of claim 65 wherein said anthranilic acid derivative is administered orally.

67. The method of claim 65 wherein said anthranilic acid derivative is administered intravenously.

* * * * *

UNITED STATES PATENT AND TRADEMARK OFFICE
CERTIFICATE OF CORRECTION

PATENT NO. : 5,789,444
DATED : August 4, 1998
INVENTOR(S) : Dennis Wonkyo Choi and Sandra Jeanne Hewett It is certified that error appears in the above-identified patent and that said Letters Patent is hereby corrected as shown below:

In Figure 7, replace "MECLOFENAMATE (µM)" with -- MEFENAMATE (µM) --.

In Column 3, line 39, replace "espeically" with -- especially --.

In Column 4, line 10, replace "mefanamic" with -- mefenamic --.

In Column 4, line 21, replace "fomula" with -- formula --.

In Column 4, line 35-36, replace "mefanamate" with --mefenamate--.

In Column 4, lines 52 and 53, delete "Dumuis et al., 1988;" and ": Rordorf et. al., 1991", respectively.

UNITED STATES PATENT AND TRADEMARK OFFICE
CERTIFICATE OF CORRECTION

PATENT NO. : 5,789,444
DATED : August 4, 1998
INVENTOR(S) : Dennis Wonkyo Choi and Sandra Jeanne Hewett It is certified that error appears in the above-indentified patent and that said Letters Patent is hereby corrected as shown below:

In Column 4, line 59, after "itself)" and before the period insert
-- (Dumuis et al., 1988; Rordorf et. al., 1991) --.

In Column 5, line 17, replace "administrering" with -- administering --.

In Column 5, line 34, delete the period immediately following "Additionally,".

Signed and Sealed this

Ninth Day of February, 1999

Attest:

Attesting Officer

*Acting Commissioner of Patents and Trademarks*